(12) United States Patent
Galichet

(10) Patent No.: US 7,258,007 B2
(45) Date of Patent: Aug. 21, 2007

(54) DEVICE FOR MEASURING THE DENSITY AND/OR SPECIFIC GRAVITY OF A LIQUID

(75) Inventor: Gilles Galichet, Troyes (FR)

(73) Assignee: Densiline, Rosieres Pres Troyes (FR)

(*) Notice: Subject to any disclaimer, the term of this patent is extended or adjusted under 35 U.S.C. 154(b) by 0 days.

(21) Appl. No.: 10/532,304

(22) PCT Filed: Oct. 20, 2003

(86) PCT No.: PCT/FR03/03096

§ 371 (c)(1),
(2), (4) Date: Oct. 18, 2005

(87) PCT Pub. No.: WO2004/038387

PCT Pub. Date: May 6, 2004

(65) Prior Publication Data

US 2006/0137448 A1 Jun. 29, 2006

(30) Foreign Application Priority Data

Oct. 22, 2002 (FR) .................................. 02 13140

(51) Int. Cl.
*G01N 9/10* (2006.01)

(52) U.S. Cl. ........................................................ 73/437

(58) Field of Classification Search .................. 73/437, 73/433, 32 R, 435, 436
See application file for complete search history.

(56) References Cited

U.S. PATENT DOCUMENTS

| 3,589,200 A * | 6/1971 | Nilsson ........................ 73/438 |
| 4,400,978 A | 8/1983 | Guay et al. |
| 4,770,041 A * | 9/1988 | Bearce ......................... 73/437 |
| 6,561,025 B2 * | 5/2003 | Ueno ........................... 73/437 |

FOREIGN PATENT DOCUMENTS

| DE | 3338311 A1 * | 5/1985 |
| DE | 90 06 275 | 8/1990 |
| FR | 2 563 339 | 10/1985 |
| FR | 2 733 318 | 10/1996 |
| WO | WO 02 01187 | 1/2002 |

* cited by examiner

*Primary Examiner*—Hezron Williams
*Assistant Examiner*—Ryan Christensen
(74) *Attorney, Agent, or Firm*—Young & Thompson

(57) ABSTRACT

A device which is used to measure the density of a liquid, includes an enclosure (1) which is impervious to the liquid to be measured. The enclosure (1) has a rigid deformation-resistant casing housing at least one reference body (3) which is suspended in the enclosure (1). The enclosure (1) can move in relation to the reference body (3) such as, in the fully submerged state, to occupy a position which is a function of the density of the liquid in which the device is submerged. In the position, the enclosure exerts a pressure or tensile force on a measuring device (2) the movement of which is limited by the reference body (3).

14 Claims, 4 Drawing Sheets

DEVICE FOR MEASURING THE DENSITY AND/OR SPECIFIC GRAVITY OF A LIQUID

The present invention relates to a device for measuring the density and/or specific gravity of a liquid, of the type comprising an enclosure impervious to the liquid to be measured.

The measurement of density takes place principally in the monitoring of continuous or discontinuous industrial processes for transformation, such as fermentation, chemical reactions with the release of gas, mixtures, emulsions or the like. Generally speaking, the devices for measuring density or specific gravity of a liquid (manual densimeter with derived flow rate, with a vibrating blade, for measuring the release of gases, etc.) have numerous drawbacks such as difficulty of reading, sensitive use, high price, high cost of installation, etc.

To overcome such drawbacks, the applicant proposed a device for measuring the density of a liquid, described in French patent application No. FR-A-2.733.318. This device comprises an enclosure of which each of the ends is closed by a flexible membrane which coacts with its internal surface with a transmission member connected to a force detector at the strain gauge, said enclosure being immersed in a vat filled with a liquid whose density is to be measured. This simple densimeter permits measuring the density of a liquid no matter what its viscosity. Nevertheless, when it is to measure a loaded liquid, which is particularly in the case of the agro-food field, this apparatus has zones of retention in which impurities can lodge. This device also has a drawback because of the positioning of the flexible membranes at each of the ends of the measuring and closure. Thus, these comprise a large surface exposed to shock and to projections and can thus be pierced during operation of manipulation of the apparatus. Finally, this apparatus has no system for protecting the force detector and thus, under the influence of an overload, the latter can give an erroneous reading of the density of the liquid, and can even deteriorate.

The applicant has moreover proposed, in an International application WO 02/01187, a device for measuring the density of a liquid comprising an enclosure impervious to the liquid to be measured, of which each of the ends is closed by a wall, these walls coacting together by means of at least one connecting member. This device is characterized in that it comprises a securement piece connected to the movable portion of a force detector with a strain gauge and secured to one of the walls, the fixed wall of the force detector remaining secured to the enclosure. Such a construction requires having an enclosure formed of several elements that can move relative to each other. These different elements of the enclosure are connected to each other by means of membranes which are urged in the course of deformation to permit the measurement of the density. This design gives rise again to the risk of premature wear of the device because of the primary role of the membranes.

Other devices for measuring the specific gravity of a liquid are moreover known from DE-U-9006275, U.S. Pat. No. 3,589,200, U.S. Pat. No. 4,400,978, FR 2.563.339 and JP 59-94036.

An object of the present invention is thus to provide a device for measuring the density and/or the specific gravity of a liquid whose design permits continuous measurement of the product and not of a removed specimen, this device being free from a deformable enclosure whose deformation would be connected to the presence of a membrane so as on the one hand to increase the precision of reading of the measurement, and on the other hand to reduce the risks of premature wear.

Another object of the present invention is to provide a measuring device whose design permits keeping the sensitive elements of the device, in particular the measurement members, such as the detector, within a sealed enclosure preventing any degradation of these latter.

Another object of the present invention is to provide a measuring device of the mentioned type, of extremely simple design, of reduced maintenance, limited wear, requiring no specialist for its installation and having extreme precision of measurement.

To this end, the invention has for its object a device for measuring the density and/or specific gravity of a liquid, of the type comprising an enclosure impervious to the liquid to be measured, characterized in that the enclosure is constituted by a rigid indeformable envelope enclosing at least one body, called a reference body, held in suspension in said enclosure in a manner totally immersed in this latter by means of at least one suspension member projecting through at least one opening of this enclosure closed in a sealed manner, this enclosure being movable relative to the reference body to occupy a totally immersed condition, a position relative to said body as a function of the density of the liquid within which the device is immersed, this position being detected and/or measured by a detection and/or measuring device disposed within the enclosure.

Thanks to the design of a measuring device of the density and/or specific gravity of a liquid in which the enclosure containing the measurement and/or detection means of the position taken by the enclosure is caused, under the influence of the Archimedes pressure exerted on said enclosure, to move relative to a reference body enclosed within the enclosure as a function of the density of the liquid in which the device is immersed, there thus results an extremely precise measurement of the density. According to a preferred embodiment of the invention, the enclosure, movable relative to the reference body to occupy a totally immersed condition, a relative position to the body as a function of the density of the liquid within which the device is immersed, encloses force measuring means, such as a force detector, this enclosure exerting, in said position, directly or by means of a piece secured to move with the enclosure, a compressive or attractive force on the force measuring means limited in displacement by the reference body, itself insensitive to the forces exerted by said enclosure.

The measurement can thus take place by means of measuring means of forces whose movement is limited by the reference body of which at least one of the surfaces constitutes, during measurement, a bearing and/or retention surface for the force measuring means, this reference body being insensitive to the forces exerted by said enclosure because of its design.

The invention will be better understood from a reading of the following description of embodiments, with reference to the accompanying drawings, in which.

Figure 1:
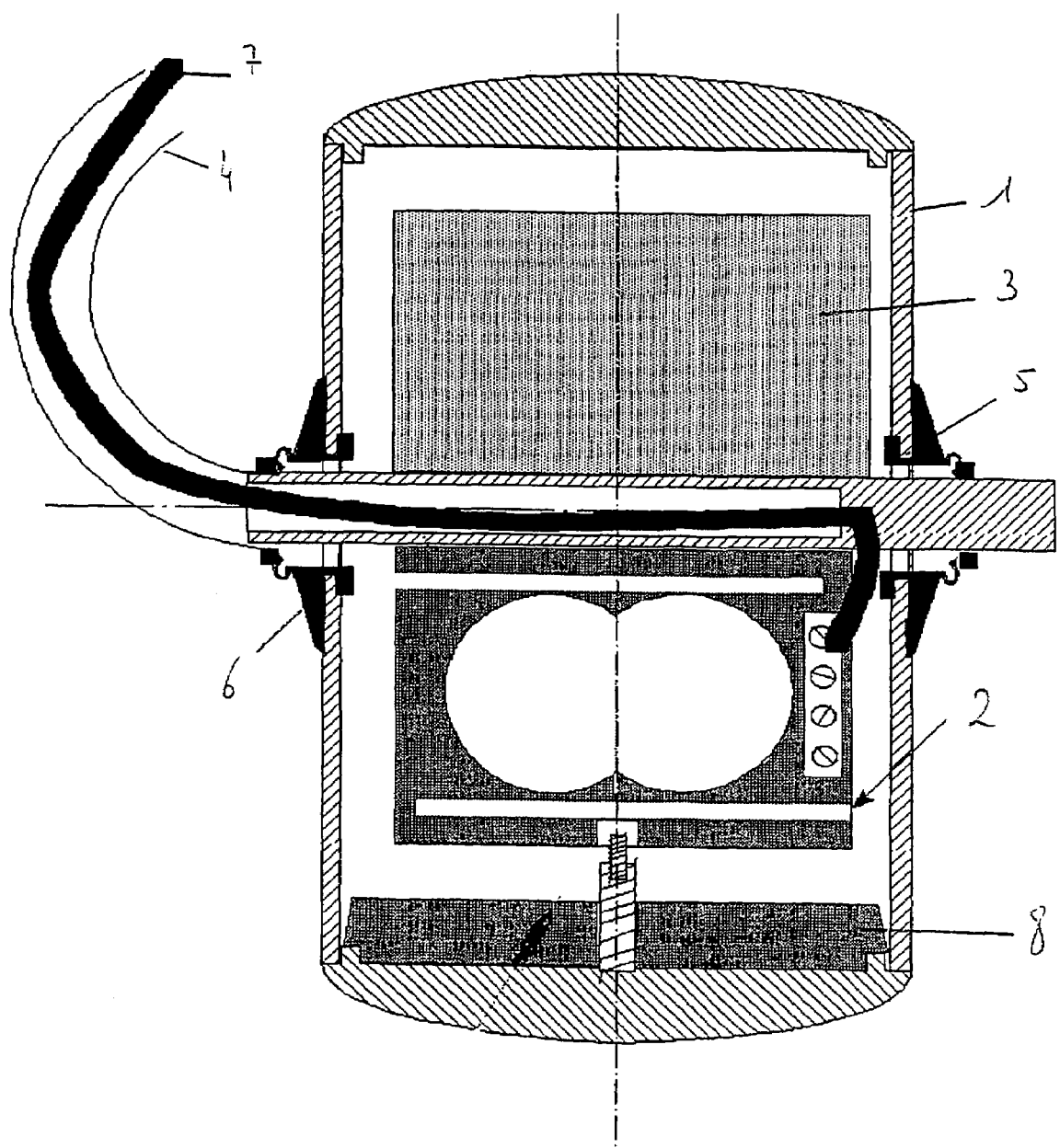
FIG. 1 is a cross-sectional view of a device according to the invention outside of a liquid.

The measuring device according to the invention permits, as mentioned above, the measurement of the density and/or the specific gravity of a liquid. This device comprises an enclosure 1 impervious to the liquid to be measured. In the illustrated embodiment, this enclosure has the form of a body of generally cylindrical appearance, preferably weighted with at least one weight 8, the weight having a function of permitting the enclosure to occupy a balanced position about the axis of the cylindrical body in the immersed condition of the device. This enclosure 1 is constituted by a rigid indeformable envelope which is preferably made of a material determined by the regulations in force in the agrifood industry. The enclosure can thus be made with PVC, stainless steel or the like. This enclosure, which thus constitutes a monobloc assembly, encloses at least one body 3, a so-called reference body, held suspended in said enclosure 1 in a totally immersed condition of this latter by means of at least one suspension member 4 projecting through at least one opening 5 closed in a sealed manner, of said enclosure 1. In the illustrated embodiments, at least one of the suspension members 4 is constituted by a tubular element for the passage of the wires necessary for the electronics of a force detector 2 also disposed within the enclosure 1. This suspension member 4 comprises preferably adjacent its connection with the reference body 3, a rigid portion. In its portion outside the device, near its securement region, this suspension member 4 extends substantially along the axis of the cylindrical enclosure 1 such that the suspension axis coincides with the longitudinal axis of the cylinder. The suspension member 4 is generally fixed by its upper portion external to the device, to the wall of a vat enclosing the liquid to be analyzed. The securement should take place such that the device will be completely immersed, that it will rest on the bottom of the vat, and that it will not be hindered in its movements by touching for example a wall.

The enclosure 1 itself comprises at least one, and preferably two, openings 5 for the passage of a suspension member 4. Each opening 5 is closed respectively by means of a membrane 6 surrounding said suspension member 4. This membrane 6 has, in its uncompressed condition, a generally conical shape. When inserted in the opening, it delimits at least one coaxial bellows with the portion of the suspension member 4 passing through the opening 5, as shown in FIG. 1. This membrane 6 permits relative movement between body 3 and enclosure 1 because of the play which it establishes at the suspension member 4. The dimensions of this membrane are thus a function of the range of movement of the enclosure relative to the reference body 3 and the amplitude of movement permitted to the enclosure.

Figure 3:
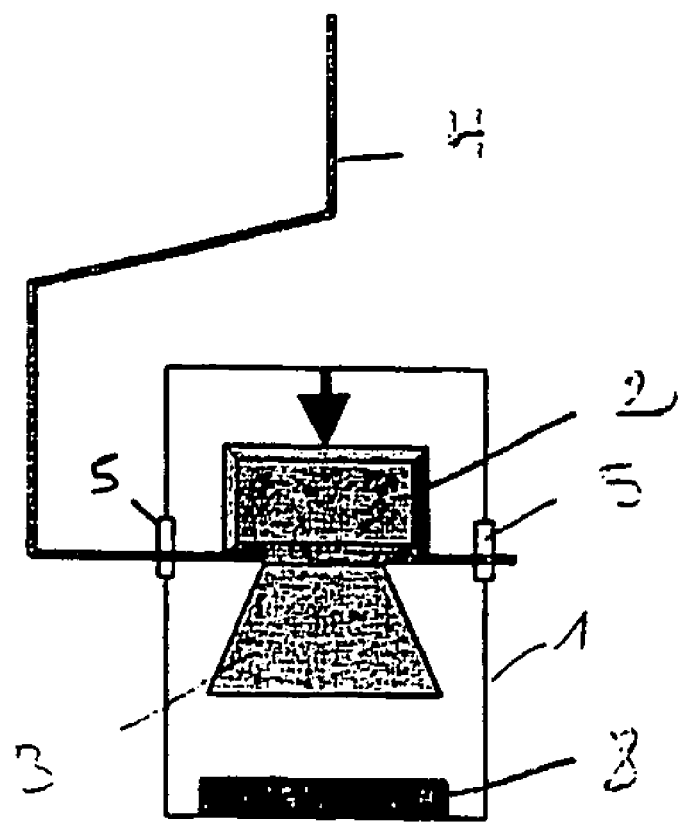
FIG. 3 is a simplified schematic view of another embodiment of the invention.
Figure 4:
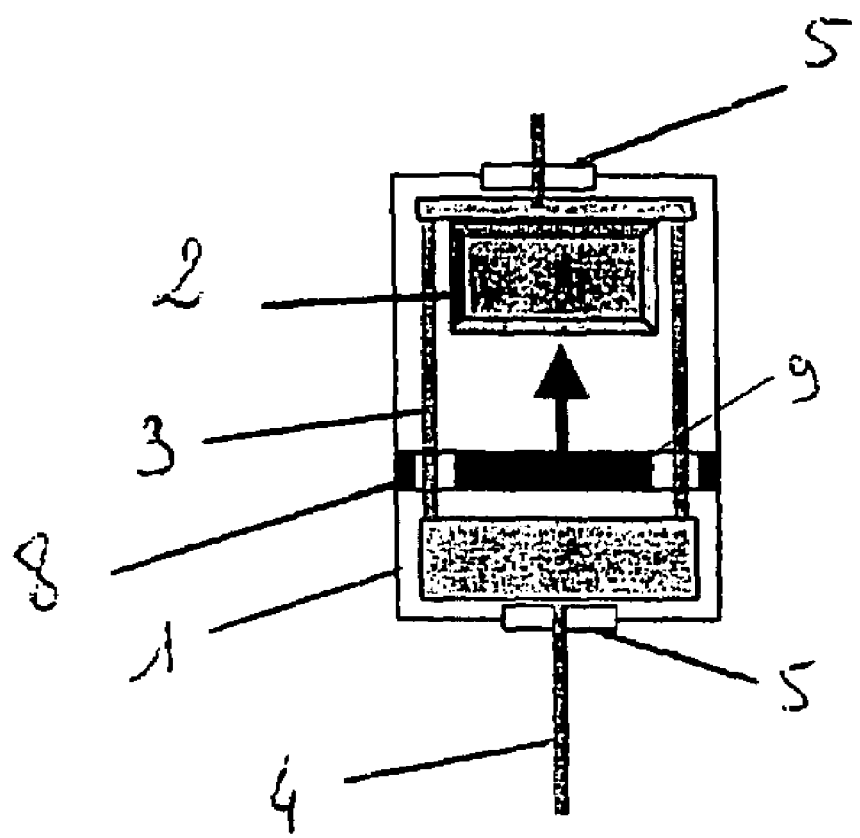
FIG. 4 is a simplified schematic view of still another embodiment of the invention.

In the case in which the enclosure comprises two passage openings 5, these are preferably provided facing each other and can be positioned on the enclosure coaxially to the vertical suspension axis of the reference body, as shown in FIG. 4. These openings 5 for passage of a suspension member 4 can also be arranged facing each other and positioned along an axis substantially perpendicular to the vertical suspension axis of the reference body 3, as shown in particular in FIGS. 1 to 3.

This enclosure 1 is thus given a relative movement with respect to the reference body 3 suspended in the enclosure in the course of its immersion in the liquid whose density is to be measured, and occupies, in the totally immersed condition, a position relative to the reference body 3 which is a function of the density of the liquid within which the device is immersed. Thus, the position taken by the enclosure 1 is a direct function of the Archimedes pressure on said enclosure. In the immersed condition, the enclosure 1 thus occupies a position resulting from the Archimedes pressure applied against said envelope of the enclosure. Means 2 for measuring and/or detecting the position taken by the enclosure 1 relative to the reference body 3 in the immersed condition of the device, are thus provided. These means 2 can have a large number of forms and generally translate the position taken by the enclosure into a variable electrical signal. In the illustrated examples, these means are constituted by measuring means of the reaction force exerted by the enclosure in the immersed position on said means 2. This force can be a compression or a tension exerted by the enclosure on the means 2 for measuring the force, limited in movement by reference body 3. These measuring means are for example constituted by a force detector 2. Other means for measuring and/or detecting the position of the enclosure, such as optical means, could be envisaged in an equivalent manner. They will not be described in more detail hereafter.

Figure 2:
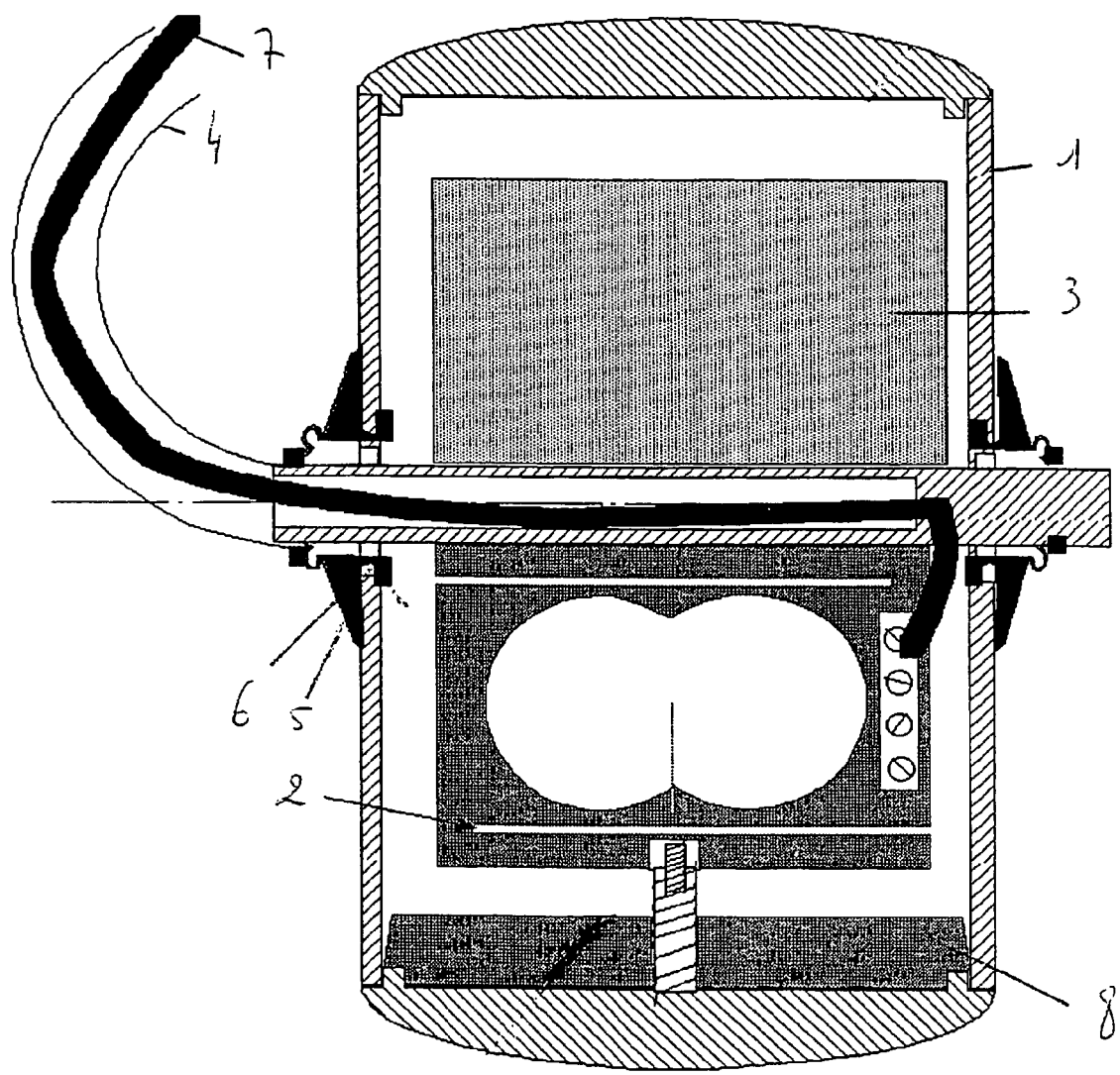
FIG. 2 is a cross-sectional view of the device of FIG. 1 in the measuring position after variation of the position relative to the enclosure with respect to the reference body.

Thus, for example, in the case shown in FIG. 2, the enclosure 1 exerts on the force detector 2, a compressive force proportional to the density of the liquid in which it is immersed. The resultant of the forces applied to the force detector 2 takes account on the one hand of the total weight of the enclosure, constituted by the weight of the envelope and of the ballast 8 when this latter is present, this ballast being secured to the envelope, and of the Archimedes pressure on the other hand, this Archimedes pressure being a function of the density of the liquid in which the device is immersed. The higher the density, the greater the Archimedes pressure. There results a greater compression of the force detector translated into a higher density. Thus the enclosure 1 exerts, in the immersed condition and as a function of the density of the liquid within which the device is immersed, a variable compression or tensile force on the detector, this detector being limited in movement by the reference body 3, itself insensitive to the forces exerted by said enclosure. This reference body 3 is thus rendered insensitive to the forces exerted by said enclosure 1, either thanks to its own weight, which is substantially greater than the forces exerted by said enclosure, or by reason of its mounting through the suspension member 4. It must thus be considered that the suspended body 3, once the device is positioned, will maintain a constant level and thereby constitute a reference for the measuring means 2.

Starting from this principle, according to which the detector or any other equivalent measuring means measures the position taken by the enclosure relative to a reference body, as a function of the density of the liquid within which the device is immersed, various embodiments can be envisaged.

Thus, in a first embodiment of the invention, in the suspended condition of the reference body 3, the force measuring means are positioned above the reference body 3 as shown in particular in FIG. 3. In this case, the force measuring means, such as a force detector, comprise a fixed portion and a movable portion, the fixed portion being coupled to the reference body 3, the movable portion to the enclosure 1. This detector can thus either be subjected to a compression force or a tensile force as a function of the direction of the force resulting from the Archimedes pressure and of the total weight of the enclosure. In the case of tensile force, a connection of the detector on the one hand to the reference body, on the other hand to the enclosure, is necessary. In the case of compression, a single connection respectively to the enclosure or to the reference body is necessary provided that the resulting force will be such that the enclosure applies itself in all cases to the detector. In the embodiment shown in FIG. 4, the enclosure exerts, by means of a piece 9, such as an internal partition secured in movement to the enclosure, a compressive force on the force detector 2.

In another embodiment of the invention according to FIGS. 1 and 2, in the suspended condition of the reference body, the force measuring means are positioned below the reference body 3. In this embodiment, the force measuring means can be secured to an internal wall of the enclosure or else the force measuring means can be secured to the reference body. These force measuring means can also be secured to an internal wall of the enclosure and secured to the reference body, the fixed portion of the force measuring means being secured to the reference body, the movable portion to the internal wall of the enclosure. FIG. 2 shows relative to FIG. 1 the position taken by the enclosure after immersion in the liquid.

Independently of their position, these force measuring means can be constituted by a strain gauge, a pressure detector, a force transmitter or a resistance for detection of forces as is well known to those skilled in this art. In the illustrated examples, the detector is a deformable body, deformed as a function of the position taken by the enclosure 1 relative to the reference body 3, this position being a direct function of the density of the liquid to be analyzed. The signals transmitted by the detector 2 translate this deformation of the detector body. To permit analysis of the results obtained from the information supplied by said detector, this detector or any other equivalent measuring means is connected to means for processing and analyzing in real time or differentially and preferably continuously the signals produced by the detector. These processing and analyzing means, not shown, can be constituted by a computer incorporating software for the acquisition and processing of data connected to said detector. Such a device can also comprise a display to express the obtained results. Generally speaking, these means convert a tension into a digital value. This device also comprises means for generating the regular supply for the detector. This device can also comprise means for measuring the temperature, this temperature being displayed simultaneously or in an alternating manner with the information relative to the density and/or specific gravity. Thus, the processing of the data permits displaying, from information relative to the density and information relative to the temperature, the specific gravity of the liquid in which the device is immersed. As a detector, there can also be used a piezoelectric detector coupled to a load converter. This configuration has the advantage of having no aging of the detector with time and provides excellent sensitivity of the detector to rapid variations and linear standardization. The use of a force detection resistance as a detector, associated with a resistance-tension converter, permits making the device particularly affordable. All these types of detectors have their advantages and their drawbacks well known to those skilled in the art.

The device for measuring density and/or specific gravity described above will preferably be used in vats having a depth less than 10 meters for measurements of the density of the liquid comprised within the range of 950 g/l-1300 g/l for temperatures varying between 15° C. and 40° C.

It is to be noted that the presence of ballast 8 of the enclosure 1 permits giving a measurement within a predetermined range and permits obtaining a reaction of the detector within a predetermined range by limiting the amplitude of movement of the enclosure.

The invention claimed is:

1. Device for measuring the density and/or specific gravity of a liquid of the type comprising an enclosure (1) impervious to the liquid to be measured,
    characterized in that the enclosure (1) is constituted by a rigid indeformable envelope enclosing at least one reference body (3), said reference body being held in suspension in said enclosure (1) in a totally immersed condition of said enclosure by means of at least one suspension member (4) projecting through said at least one opening (5) closed in a sealed manner, of said enclosure (1), this enclosure (1) being movable relative to the reference body (3) to occupy, in the totally immersed condition of the enclosure, a position relative to the body (3) as a function of the density of the liquid within which the device is immersed, this position being detected and/or measured by detection and/or measurement means (2) disposed within the enclosure (1).

2. Measuring device according to claim 1, characterized in that the enclosure (1), movable relative to the reference body (3) to occupy, in the totally immersed position, a position relative to the body (3) as a function of the density of the liquid within which the device is immersed, encloses means (2) for measuring force, such as a force detector, this enclosure exerting, in said position, directly or by means of a piece (9) secured to move with the enclosure, a compressive or tensile force on said means (2) for measuring forces limited in dispersement by the reference body (3), itself insensitive to the forces exerted by said enclosure (1).

3. Measuring device according to claim 2,
    characterized in that, in the suspended condition of the reference body (3), the force measuring means (2) are positioned above the reference body (3).

4. Measuring device according to claim 2,
    characterized in that, in the suspended condition of the reference body (3) the force measuring means (2) are positioned below the reference body (3).

5. Measuring device according to claim 2,
    characterized in that the force measuring means are constituted by a force detector (2) comprising a fixed portion and a movable portion, the fixed portion being coupled to the reference body (3), the movable portion being coupled to the enclosure (1).

6. Measuring device according to claim 2,
    characterized in that the force measuring means (2) is secured to an internal wall of the enclosure (1).

7. Measuring device according to claim 2,
    characterized in that the force measuring means (2) are secured to the reference body (3).

8. Measuring device according to claim 1,
    characterized in that the enclosure (1) comprises at least two openings (5) for the passage of a suspension member, each opening (5) being closed respectively by means of a membrane (6) surrounding said suspension member (7).

9. Measuring device according to claim 8,
    characterized in that the openings (5) for passage of a suspension member are arranged facing each other and are positioned on the enclosure in a manner coaxial with the vertical axis of suspension of the reference body (3).

10. Measuring device according to claim 8, characterized in that the openings (5) for passage of a suspension member are arranged facing each other and are positioned on an axis substantially perpendicular to the vertical axis of suspension of the reference body (3).

11. Measuring device according to claim 1, characterized in that at least one of the suspension members (4) is constituted by a tubular element for the passage of wires necessary for the electronics of the measuring means (2).

12. Measuring device according to claim 1, characterized in that the enclosure (1) has a generally cylindrical shape, preferably ballasted.

13. Measuring device according to claim 1, characterized in that the measuring and/or detecting means (2) are connected to means for processing and analyzing in real time or differentiated and preferably continuously, the signals produced by said measuring means (2).

14. Measuring device according to claim 2, characterized in that the force measuring means (2) are constituted by a deformable body deformed as a function of the position taken by the enclosure (1) with respect to the reference body (3), this position being a direct function of the density of the liquid to be analyzed.

* * * * *